(12) United States Patent
Ripich

(10) Patent No.: US 7,029,484 B2
(45) Date of Patent: Apr. 18, 2006

(54) TONGUE CLEANING DEVICE

(75) Inventor: Robert J. Ripich, Canton, OH (US)

(73) Assignee: Biocurv Medical Instruments, Inc., Canton, OH (US)

( * ) Notice: Subject to any disclaimer, the term of this patent is extended or adjusted under 35 U.S.C. 154(b) by 488 days.

(21) Appl. No.: 10/038,563

(22) Filed: Jan. 3, 2002

(65) Prior Publication Data

US 2002/0128673 A1 Sep. 12, 2002

Related U.S. Application Data

(60) Provisional application No. 60/259,655, filed on Jan. 4, 2001.

(51) Int. Cl.
*A61B 17/24* (2006.01)

(52) U.S. Cl. ..................................... 606/161
(58) Field of Classification Search ................ 606/161, 606/160; 15/111, 104.1
See application file for complete search history.

(56) References Cited

U.S. PATENT DOCUMENTS

| | | |
|---|---|---|
| 619,466 A | 2/1899 | Buchmann |
| 781,292 A | 1/1905 | Murphree |
| 856,711 A | 6/1907 | Lees |
| 872,567 A | 12/1907 | Langstaff |
| 1,811,775 A | 6/1931 | Barkwill |
| 3,491,747 A | 1/1970 | Robinson |
| 3,502,082 A | 3/1970 | Chatfield |
| 3,890,964 A | 6/1975 | Castanedo |
| D242,744 S | 12/1976 | Rendleman et al. |
| 4,043,322 A | 8/1977 | Robinson |
| D246,878 S | 1/1978 | Kitzis |
| D265,506 S | 7/1982 | Finamore |
| 4,455,704 A | 6/1984 | Williams |
| 4,488,327 A | 12/1984 | Snider |
| D291,001 S | 7/1987 | Gaskins |
| D295,343 S | 4/1988 | Regalado |
| D295,695 S | 5/1988 | Golzari |
| D301,372 S | 5/1989 | Tsen |
| D303,426 S | 9/1989 | Simonian |
| 4,875,496 A | 10/1989 | Prabhudass |
| 5,061,272 A | 10/1991 | Reese |
| D324,912 S | 3/1992 | Hansen |
| 5,217,475 A | 6/1993 | Kuber |
| 5,226,197 A | 7/1993 | Nack et al. |
| 5,282,814 A | 2/1994 | Srivastava |
| D360,262 S | 7/1995 | Ly |
| D367,707 S | 3/1996 | Baker |
| 5,530,981 A | 7/1996 | Chen |
| 5,624,259 A * | 4/1997 | Heath et al. ............. 433/72 |

(Continued)

OTHER PUBLICATIONS

The OraFresh Homepage.

*Primary Examiner*—Eduardo C. Robert
*Assistant Examiner*—Jessica R. Baxter
(74) *Attorney, Agent, or Firm*—Zollinger & Burleson Ltd.

(57) ABSTRACT

A tongue cleaning device includes a debris retention feature that helps the user remove debris from the tongue. In one embodiment, the feature is a suction system that removes the debris from the working area of the device. In another embodiment, the feature is a recess positioned adjacent the working edge such that the debris will collect in the recess. Another embodiment of the invention provides a tongue cleaning device having a working edge that is concave with respect to the tongue. Other embodiments of the invention provide flexible handle and head designs.

14 Claims, 13 Drawing Sheets

U.S. PATENT DOCUMENTS

| | | |
|---|---|---|
| 5,893,860 A | 4/1999 | Ripich et al. |
| 5,916,228 A | 6/1999 | Ripich et al. |
| 6,015,293 A * | 1/2000 | Rimkus .................. 606/161 |
| 6,451,038 B1 | 9/2002 | Rosenblood et al. |
| 2002/0091400 A1 | 7/2002 | Harold |
| 2002/0107537 A1 | 8/2002 | Singh |
| 2002/0166191 A1 | 11/2002 | Josdal |
| 2003/0083680 A1 | 5/2003 | Jousson |
| 2003/0115699 A1 | 6/2003 | Wagstaff |
| 2003/0116884 A1 | 6/2003 | Wagstaff |
| 2003/0167582 A1 | 9/2003 | Fischer et al. |
| 2003/0216762 A1 | 11/2003 | Levit |

* cited by examiner

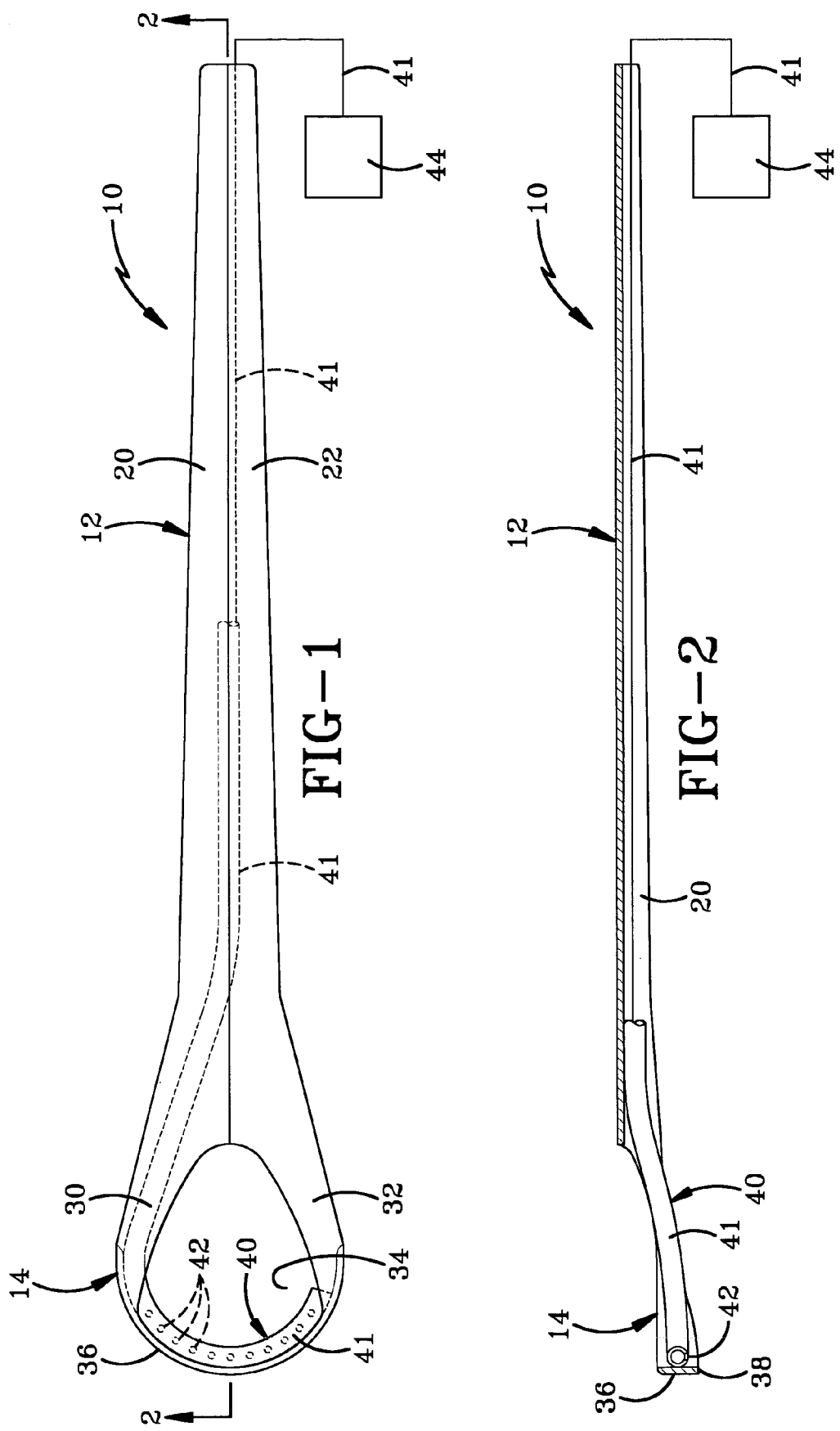

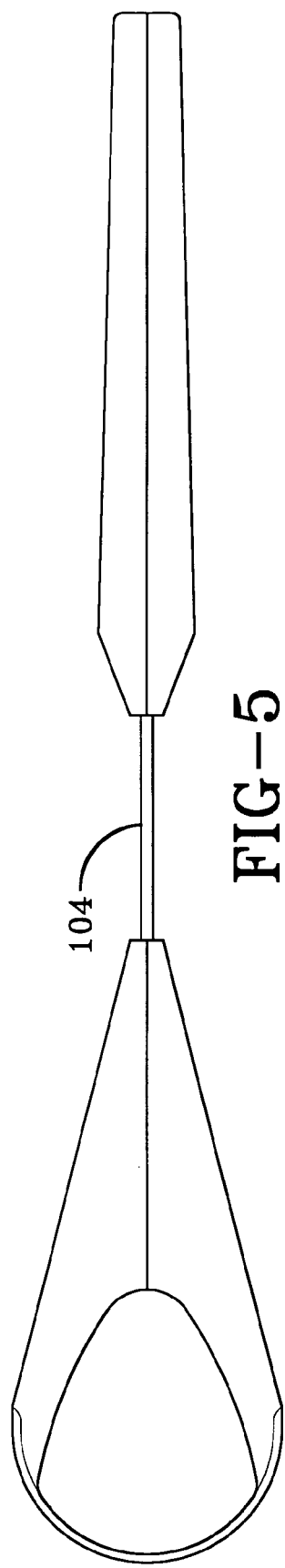
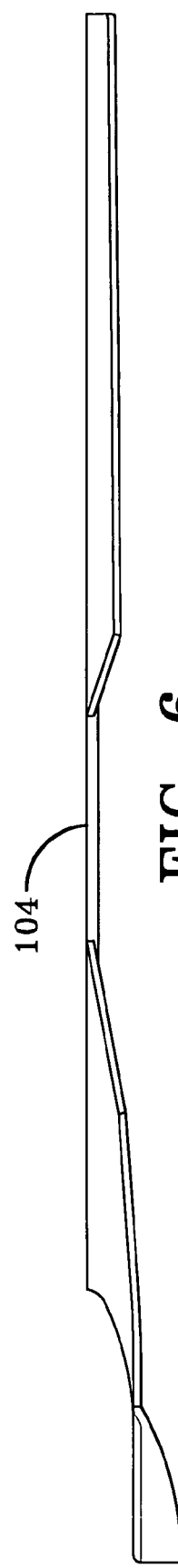

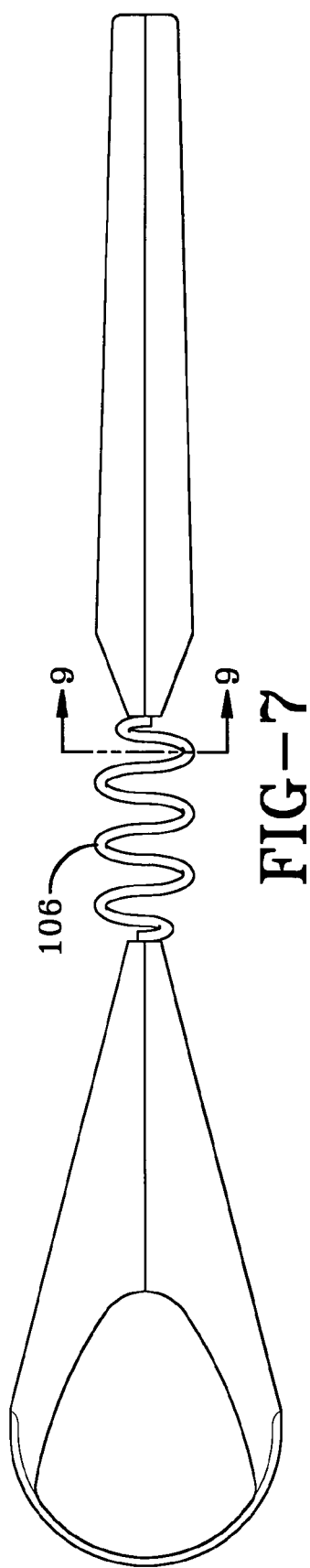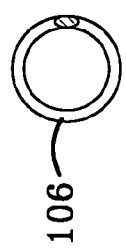

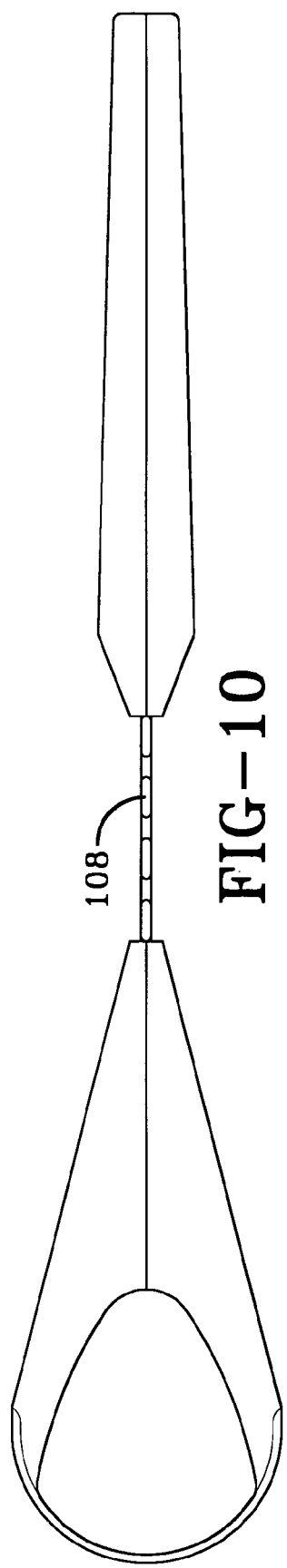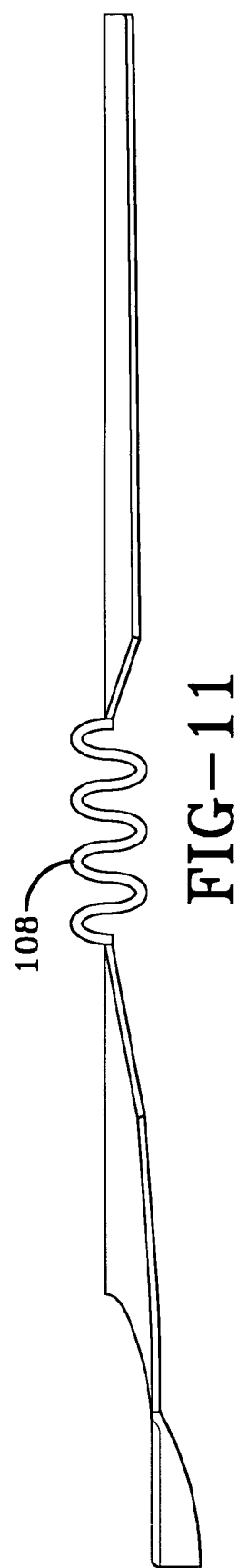

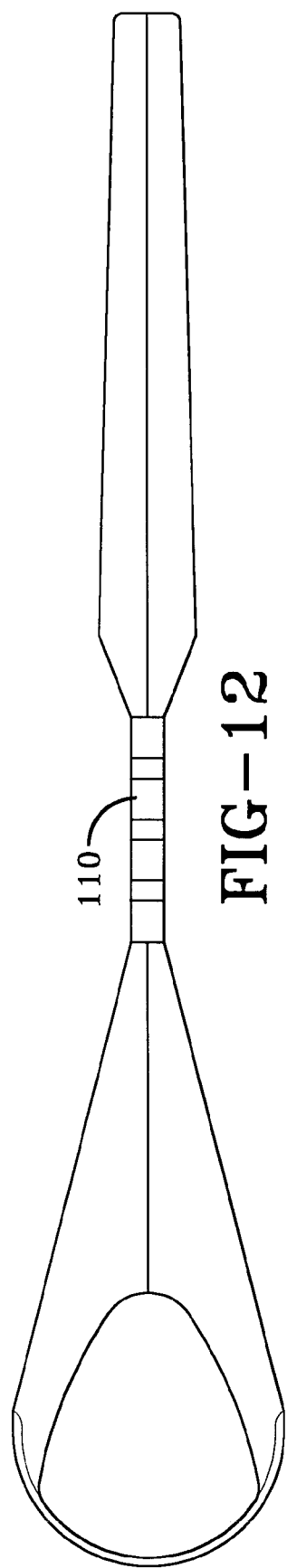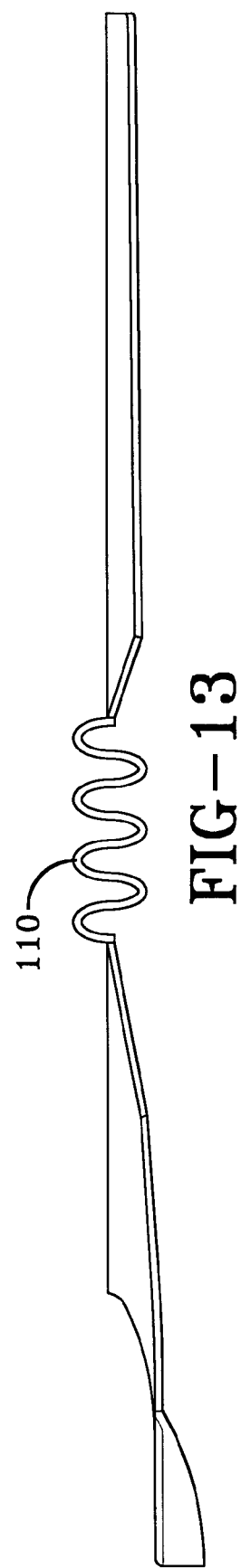

FIG-23
A  B  C  D  E  F  G  H
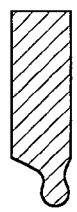 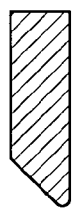 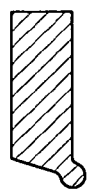 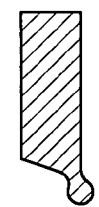 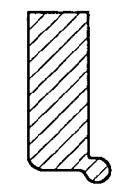 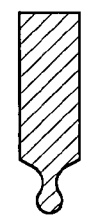 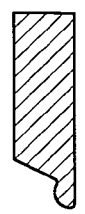 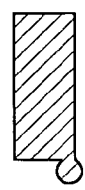
I  J  K  L  M  N  O  P
      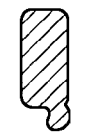 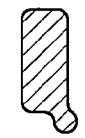
Q  R  S  T  U  V  W  X
  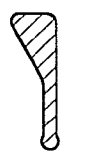 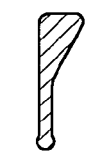    

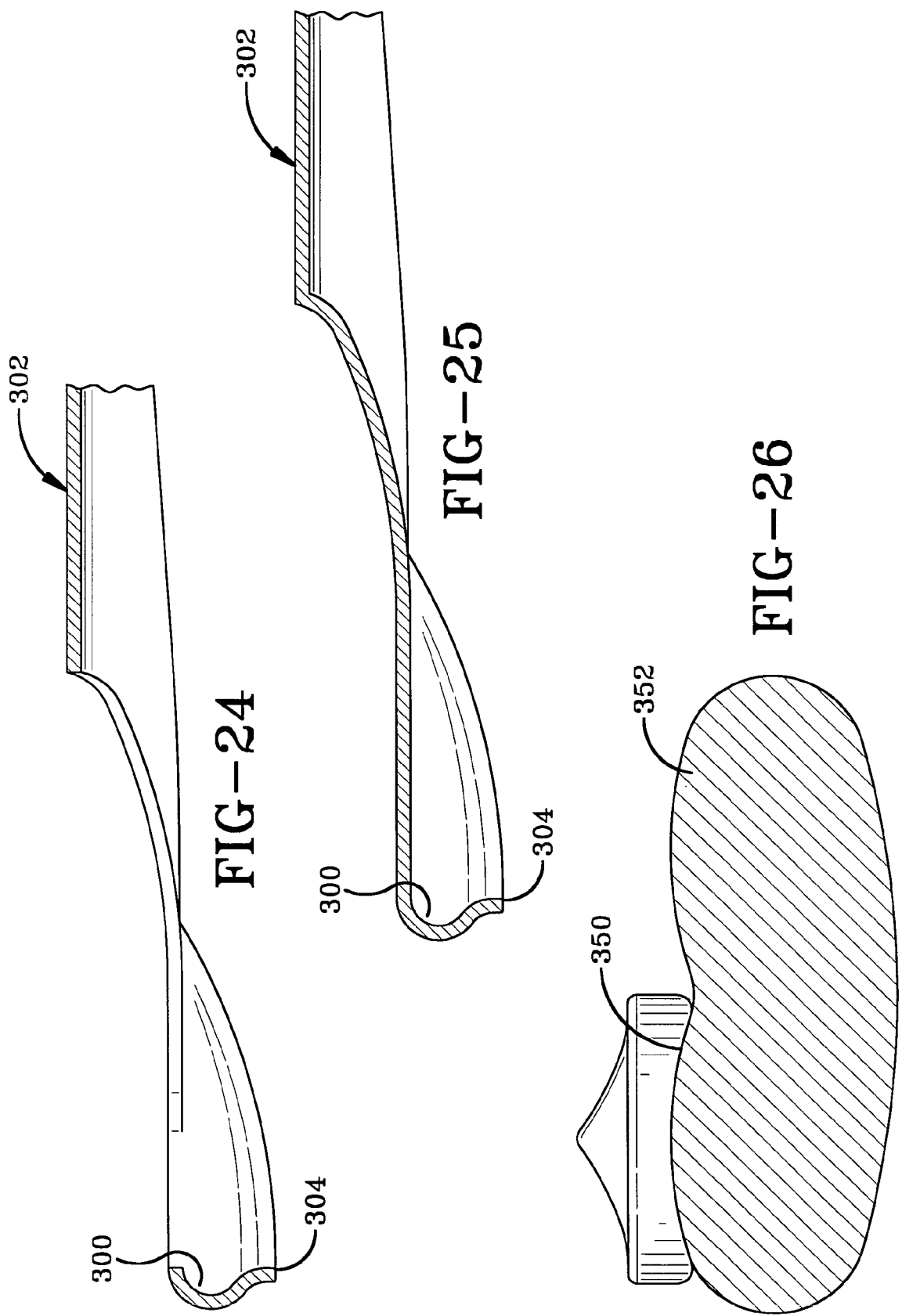

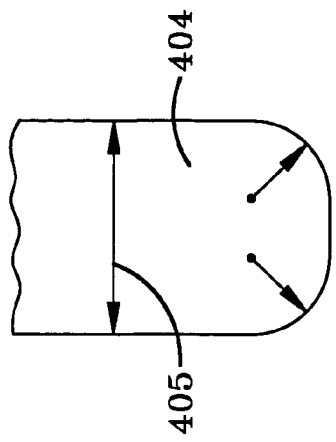
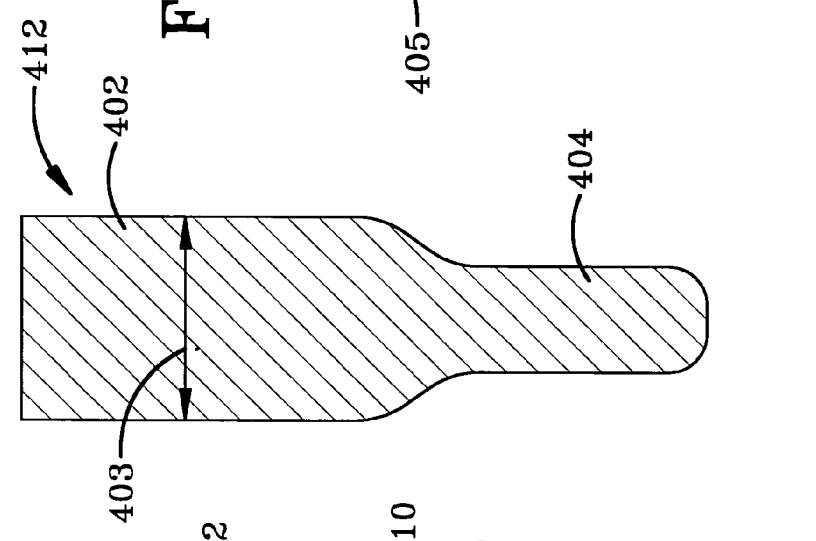
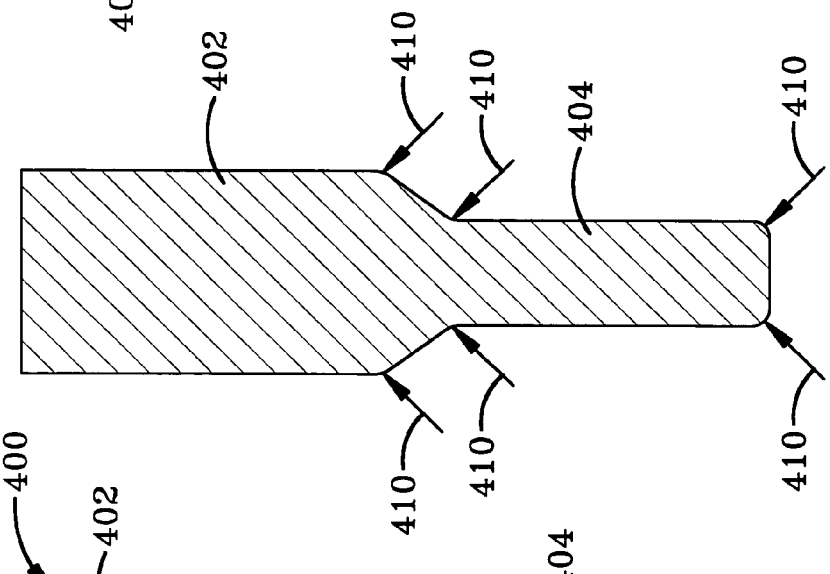
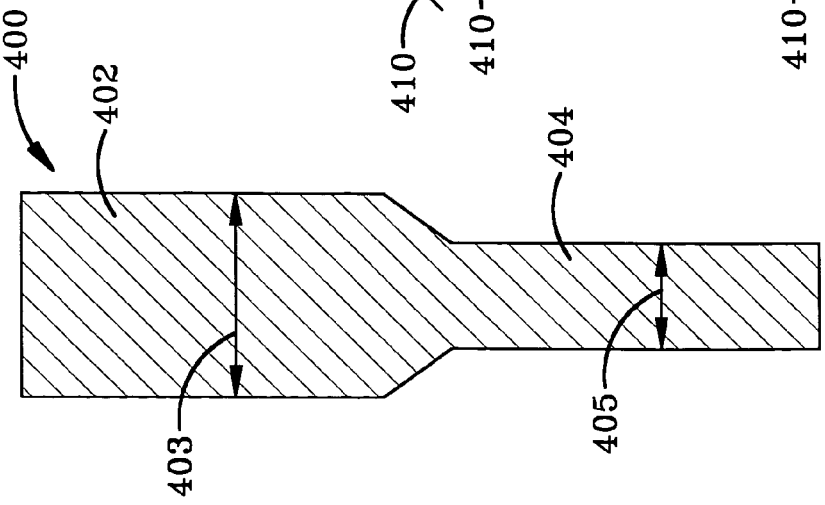

TONGUE CLEANING DEVICE

CROSS REFERENCE TO RELATED APPLICATIONS

This application claims priority from U.S. Provisional Patent Application Ser. No. 60/259,655 filed Jan. 4, 2001; the disclosures of which are incorporated herein by reference.

BACKGROUND OF THE INVENTION

1. Technical Field

The present invention generally relates to tongue cleaning devices.

2. Background Information

Numerous types of tongue cleaning devices are known in the art. All have advantages and disadvantages. The art generally desires a tongue cleaning device that effectively cleans the plaque and debris from the tongue while being safe, easy to use, and effective.

One drawback with existing tongue cleaning devices is that the debris collected by the device will fall off of the device shortly after the device is removed from the tongue. Most home users clean their tongues over a bathroom sink and the debris retention problem does not bother them or stop them from using the devices. In other settings, the debris retention problem is of more concern. One such setting is a hospital where it is becoming more desirable to clean the tongues of bedridden patients in order to reduce the amount of bacteria of the patient's tongue. Those who use tongue cleaning devices in these situations desire a tongue cleaning device that will retain or remove the debris from the scraping wall of the tongue cleaning device so that the tongue cleaning device may be easily used on a patient who is on his back.

Another problem in the tongue cleaner art is the manufacture of the working edge for the tongue cleaner. A working edge cannot be too sharp because the edge will cut the tongue. On the other hand, the working edge cannot be too dull because the edge will not clean the tongue. The art thus desires tongue cleaning designs and methods for manufacturing tongue cleaning devices wherein the sharpness of the working edge can be controlled.

A further drawback with known tongue cleaning devices is the amount of tongue width that can be effectively cleaned by a single pass of the tongue cleaning device. The art desires a working edge shape and configuration that more effectively cleans the surface of the tongue.

The art also desires flexible tongue cleaning devices that flex when pressed down on the tongue to help prevent the user from pressing too hard against the tongue. To be useful, the handle must flex along the longitudinal axis of the handle. The art desires different handle and head configurations that provide for this flexing motion.

SUMMARY OF THE INVENTION

One embodiment of the invention provides a tongue cleaning device that allows the debris being gathered by the tongue cleaning device to be easily removed from the tongue and device. The embodiment provides for easy debris removal by combining a suction mechanism with the tongue scraping member. The suction mechanism may be a powered suction mechanism or a manual suction mechanism. The elements of the suction mechanism may be replaceable.

Another embodiment of the invention provides a tongue cleaning device that incorporates a debris retention feature that retains the debris collected from the tongue.

Another embodiment of the invention provides a tongue cleaning device that incorporates a working edge that is concave with respect to the tongue so that a wide section of the tongue may be cleaned with a single pass of the device.

Another embodiment of the invention provides a tongue cleaning device having a flexible handle. The flexible handle allows the working blade of the tongue cleaning device to be properly positioned on the tongue during use. The invention provides a flexible handle that has memory so that it returns to its original resting position after each use.

Another embodiment of the invention provides a tongue cleaning device fabricated from titanium. In one embodiment, the titanium is anodized to provide different colors to the tongue cleaning device.

Another embodiment of the invention provides a tongue cleaning device having a scraping member with a smooth working edge that always presents a rounded surface to the user's tongue. The rounded surface prevents the working edge from catching on the user's tongue during use.

BRIEF DESCRIPTION OF THE DRAWINGS

FIG. 1 is a top plan view of a tongue cleaning device having a suction mechanism to remove debris scraped from the tongue surface.

FIG. 2 is a sectional view taken along line 2—2 of FIG. 1.

FIG. 5 is a top plan view of a tongue cleaning device having a flexible handle.

FIG. 6 is a side view of FIG. 5.

FIG. 7 is a top plan view of a tongue cleaning device having a flexible handle.

FIG. 8 is a side view of FIG. 7.

FIG. 9 is a sectional view taken along line 9—9 of FIG. 7.

FIG. 10 is a top plan view of a tongue cleaning device having a flexible handle.

FIG. 11 is a side view of FIG. 10.

FIG. 12 is a top plan view of a tongue cleaning device having a flexible handle.

FIG. 13 is a side view of FIG. 12.

FIGS. 23A–23X depict different scraping member cross sections that may be used with different tongue cleaning devices.

FIG. 24 is a section view of the head of a tongue cleaning device with a debris retention recess.

FIG. 25 is a section view of an alternative tongue cleaning device head having a debris retention recess similar to the head in FIG. 24.

FIG. 26 shows an end view of a tongue cleaning device showing a working edge having a concave shape with respect to the tongue.

FIG. 28 is a section view of a scraping wall of a tongue cleaning device before it is polished to round the corners.

FIG. 29 is a section view of the wall of FIG. 28 showing the polishing forces acting on the wall.

FIG. 30 is a section view of the wall of FIG. 28 showing the scraping wall after it has been polished.

FIG. 30A is an enlarged view of the working edge of the scraping wall.

Similar numbers refer to similar parts throughout the specification.

DETAILED DESCRIPTION OF THE DRAWINGS

Figure 3:
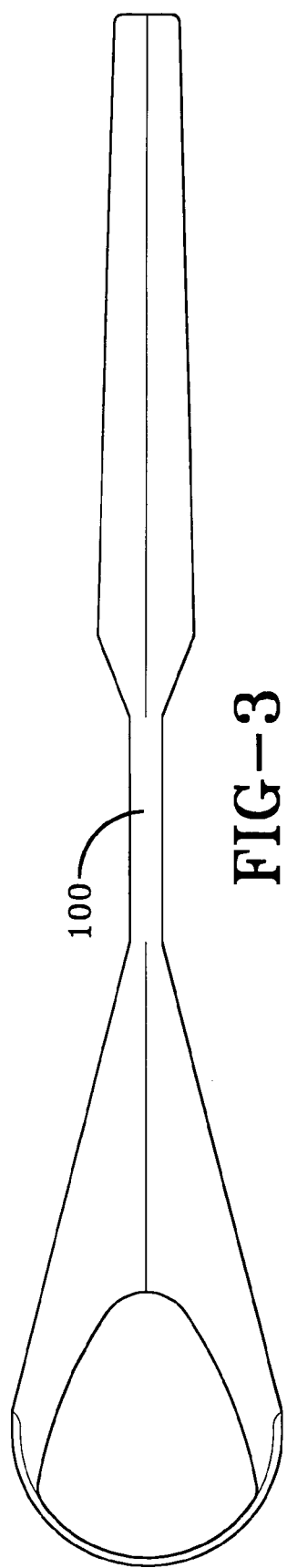
FIG. 3 is a top plan view of a tongue cleaning device having a flexible handle.

One embodiment of the tongue cleaning device of present invention is indicated generally by the numeral 10 in FIGS. 1 and 2. Tongue cleaning device 10 generally includes body that has a handle 12 and a head 14. Handle 12 is an elongated structure that fits the human hand so that the user may manipulate head 14 with handle 12. Head 14 generally includes an edge that engages the user's tongue and removes the debris from the user's tongue.

In the embodiment of the invention depicted in FIGS. 1 and 2, handle 12 has a V-shaped cross section that includes opposed sides 20 and 22. The V-shaped cross section adds strength to the handle and provides a handle that is easy to grip by the user.

Handle 12 terminates into head 14. Specifically, the exemplary head 14 includes a pair of legs 30 and 32 that each split off substantially longitudinally and in a substantially planar manner from its respective side 20 and 22. An opening 34 is disposed between legs 30 and 32. Head 14 may be slightly angled from the longitudinal axis of handle 12 as is shown in FIG. 2. Different heads 14 may be used in other embodiments of the invention.

A scraping member or wall 36 extends between the outer ends of each leg 30 and 32 transversely to legs 30 and 32. Scraping wall 36 may be curved. When in use, scraping wall 36 is substantially vertical while handle 12 and legs 30 and 32 are substantially horizontal. The lowermost edge of scraping wall 36 is the working edge 38 that engages the tongue. Working edge 38 is smooth in the drawings while it may be jagged, tooth, serrated, grooved, notched, stepped, or otherwise patterned in other embodiments. In each of these embodiments, the sharpness of working edge 38 is dull enough to avoid cutting the user's tongue while in use.

Tongue cleaning device 10 includes a debris-removal system 40 adapted to remove debris from device 10 that device 10 has collected from the user's tongue. System 40 includes a channel 41 that allows debris to be transported away from head 14. Channel 41 terminates adjacent working edge 38 or scraping wall 36. A single or a plurality of openings 42 provide communication between channel 41 and working edge 38. Channel 41 may extend from working edge 38, down head 14, and along handle 12. Channel 41 is in fluid communication with a vacuum source 44 that provides a suction force to openings 42. The suction force is sufficient to transport debris being removed from the tongue by working edge 38 through channel 41. Suction device 44 may be a powered suction device that is commonly used in a dentist office. In this embodiment, the debris removed by tongue cleaning device 10 is automatically deposited in an appropriate receptacle by the powered suction device. In another embodiment, suction device 44 may be a manually-activated bulb that is selectively connected to channel 41. In this embodiment, the user depresses the bulb and releases the bulb to create the suction force as he applies working edge 38 to his tongue.

Channel 41 may be removably attached or integrally formed with head 14 and handle 12. When removably attached, channel 41 may be cleaned and re-attached. Channel 41 may also be easily replaced. When integrally formed, channel 41 is configured to allow the interior of channel to be cleaned by appropriate cleaning techniques known in the dentistry art.

Opening 42 may be centrally positioned with respect to head 14. In other embodiments, openings 42 are disposed along the length of working edge 38 and/or legs 20 and 22. When a plurality of openings are used, each opening 42 may be connected to channel 41 with an individual channel so that the suction force is evenly distributed to each opening 42.

Tongue cleaning device 10 may be fabricated from a variety of materials known in the art such as plastic, steel, aluminum, titanium, etc. The material may be cleaned and sterilized. For home use, the material may withstand the heat of a standard dishwasher. The material may have a non-porous finish that does not allow organic material to collect on the surface.

Figure 27:
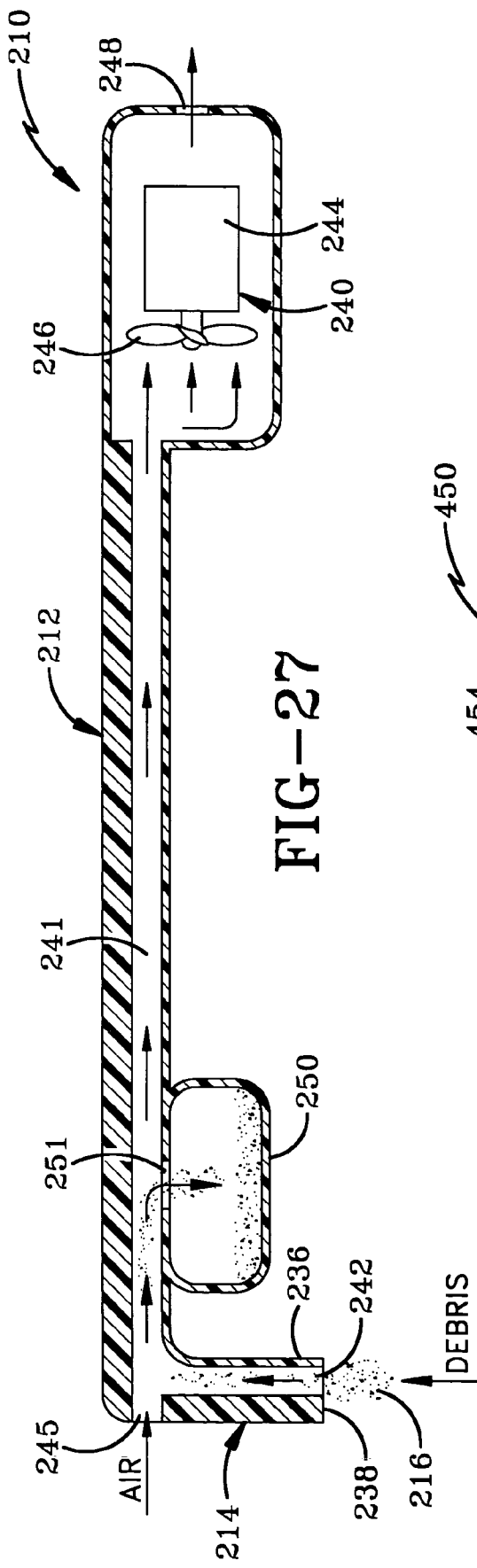
FIG. 27 is a section view of a tongue cleaning device that has a self-contained debris removal system.

An alternative embodiment of a tongue cleaning device having a suction system is indicated generally by the numeral 210 in FIG. 27. Tongue cleaning device 210 generally includes body that has a handle 212 and a head 214. Handle 212 is an elongated structure that fits the human hand so that the user may manipulate head 214 with handle 212. Head 214 generally includes an edge that engages the user's tongue and removes the debris 216 from the user's tongue.

In the embodiment of the invention depicted in FIG. 27, handle 212 is a straight, elongated handle sized to be held by and manipulated with the human hand. Handle 212 terminates into head 214 that defines a scraping member or wall 236 that extends down from handle 214. The lowermost edge of scraping wall 236 is the working edge 238 that engages the tongue.

Tongue cleaning device 210 includes a debris-removal system 240 adapted to remove debris from device 210 that device 210 has collected from the user's tongue. System 240 includes a channel 241 that allows debris to be transported away from head 214. Channel 241 terminates adjacent working edge 238 or scraping wall 236. A single or a plurality of openings 242 provide communication between channel 241 and working edge 238. Channel 241 may extend from working edge 238, down head 214, and along handle 212. Channel 241 is in fluid communication with a vacuum source 244 that provides a suction force to opening 242. The suction force is sufficient to transport debris being removed from the tongue by working edge 238 through channel 241. A venturi opening 245 is provided in head 214 to create a suction flow through opening 242 without causing device 210 from suctioning itself to the user's tongue. Venturi opening 245 is in fluid communication with channel 241.

Suction device 244 is a powered suction device having a fan 246 disposed in a housing 247 carried by handle 212. Fan 246 blows air out of an exhaust opening 248 defined by housing 247. Appropriate switches and power sources may be supplied as needed to operate device 244.

In this embodiment, the debris removed by tongue cleaning device 210 is deposited in an appropriate debris retention device 250. Device 250 may be removable so that it may be cleaned or replaced. In some embodiments, device 250 may be disposable. Device 250 is positioned intermediate working edge 238 and suction device such that debris pulled into channel 241 is dropped into device 250 through opening 251 before it reaches suction device 244.

Channel 241 and suction device 244 may be removably attached or integrally formed with head 214 and handle 212.

Opening 242 may be centrally positioned with respect to head 214. In other embodiments, openings 242 are disposed along the length of working edge 238. When a plurality of openings are used, each opening 242 may be connected to channel 241 with an individual channel so that the suction force is evenly distributed to each opening 242.

Different embodiments of tongue cleaning devices are depicted in FIGS. 3–22. Each of the tongue cleaning devices in FIGS. 3–22 include a flexible handle design that allows head 14 to flex with respect to the end of handle 12. In each of these embodiments, the flexible handle has a memory that causes the handle to return to its original position after being bent.

Figure 4:
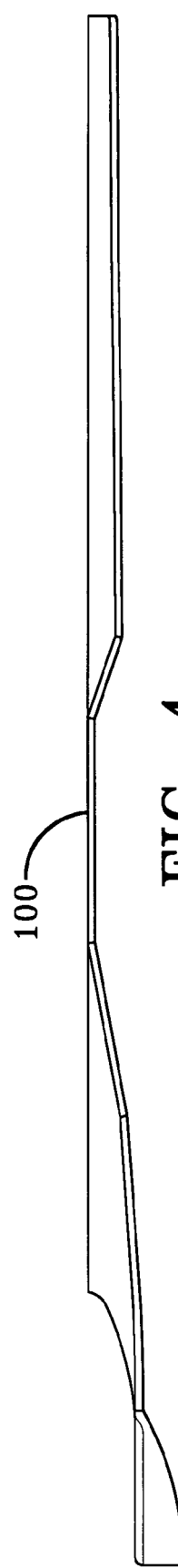
FIG. 4 is a side view of FIG. 3.

In FIGS. 3 and 4, the handle of the tongue cleaning device includes a relatively thin, flat section 100 that allows the head of the tongue cleaning device to flex with respect to the portion of the handle gripped by the user. Section 100 may be substantially flat or may have the same V-shaped cross section as the handle. In either configuration, the width of section 100 is substantially thinner than the remaining portion of the handle. The width of section 100 may be 50 percent less than the width of the portions of the handle disposed immediately adjacent section 100. In other embodiments, the width may be ⅔ less.

Figure 3A:
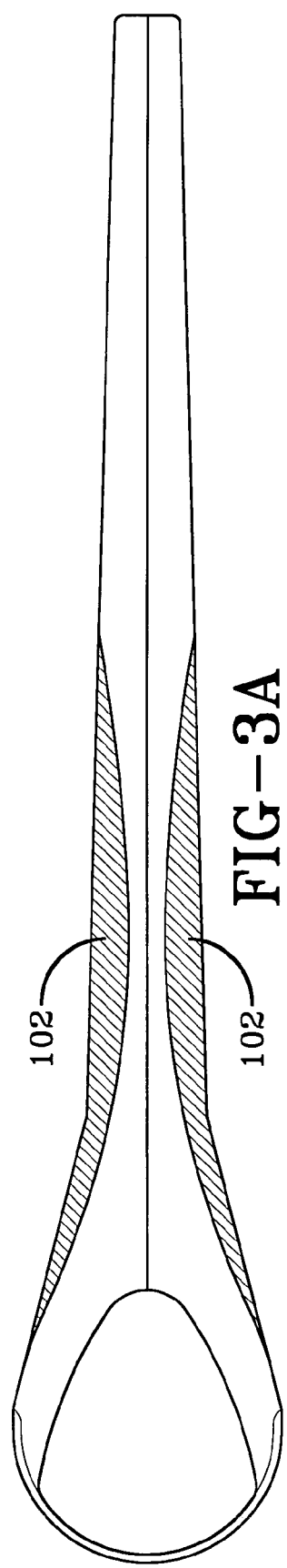
FIG. 3A is a view similar to FIG. 3 showing an alternative embodiment of the flexible handle.

Another embodiment is depicted in FIG. 3A wherein material is removed from both the handle and the head as indicated by the shaded sections 102. In this embodiment, the thin section of the handle smoothly curves and flows into both the head and the handle of the tongue cleaning device. In the embodiments of FIGS. 3 and 3A, the thin section of the handle is referred to as the neck of the handle. The thin neck allows the head of the device to flex with respect to handle.

In FIGS. 5 and 6, the neck of the handle is formed with a round rod 104 that is used to connect the handle with the head. The rod is flexible so that the head may flex with respect to the handle. The rod may be provided in a variety of different configurations and may be fabricated from different materials to increase or decrease its flexibility.

In FIGS. 7–9, the handle is connected to the head with a coil spring 106 that allows the head to flex with respect to the handle.

In FIGS. 10 and 11, a spring 108 having a wave-shaped configuration is used to provide the flexing between the head and the handle. The side view depicted in FIG. 11 shows the wave-shaped pattern of spring 108. Spring 108 has a round cross section.

In FIGS. 12 and 13, a spring 110 is used to provide the flexibility. Spring 110 has a wave-shaped pattern similar to spring 108. Spring 110 has a flat cross section.

Figure 14:
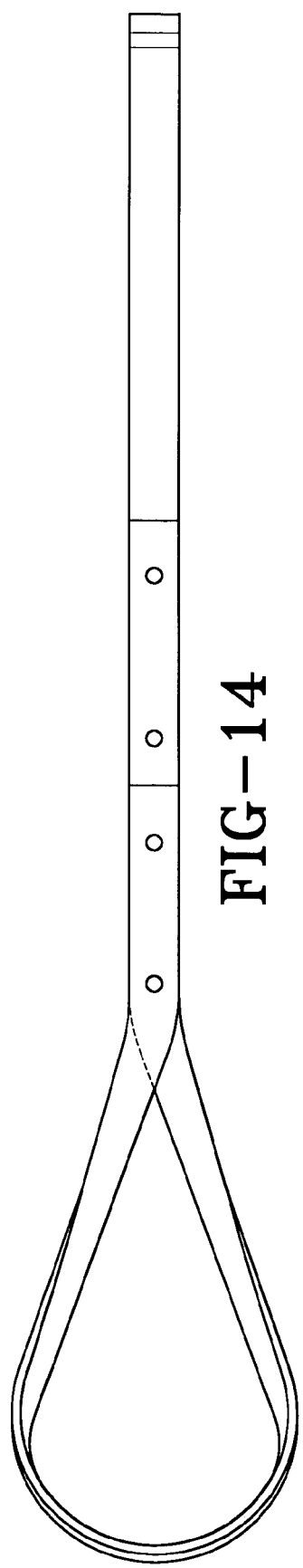
FIG. 14 is a top plan view of a tongue cleaning device having a flexible handle.
Figure 15:
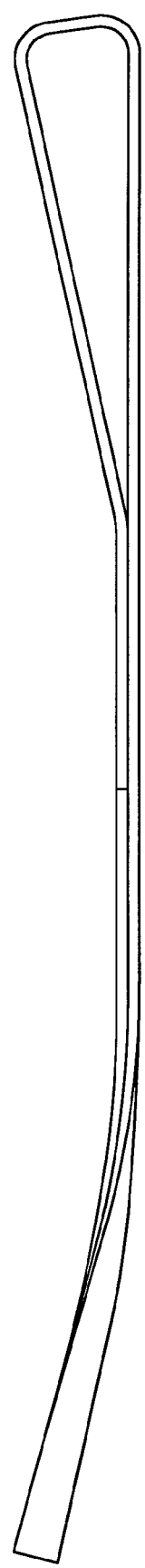
FIG. 15 is a side view of FIG. 14.

FIGS. 14 and 15 show another embodiment wherein the handles of the tongue cleaning device includes two lengths of material disposed substantially parallel to one another. This structure is shown in U.S. Pat. No. 5,916,228 in FIGS. 16–18. The handle structure depicted in FIGS. 14 and 15 allows the head of the tongue cleaning device to flex with respect to the handle. The welds depicted in FIG. 14 may be added to increase the stiffness of the handle. The welds may be eliminated to decrease the stiffness of the handle.

Figure 16:
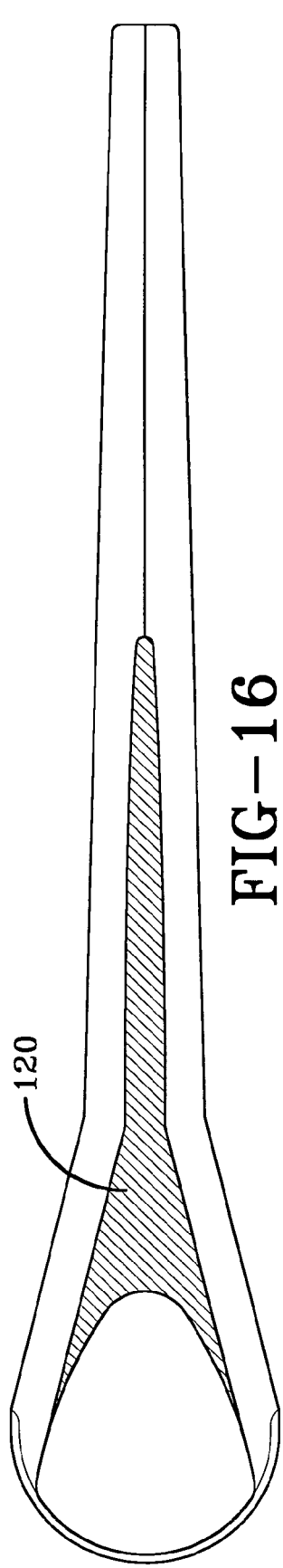
FIG. 16 is a top plan view of a tongue cleaning device having a flexible handle.
Figure 17:
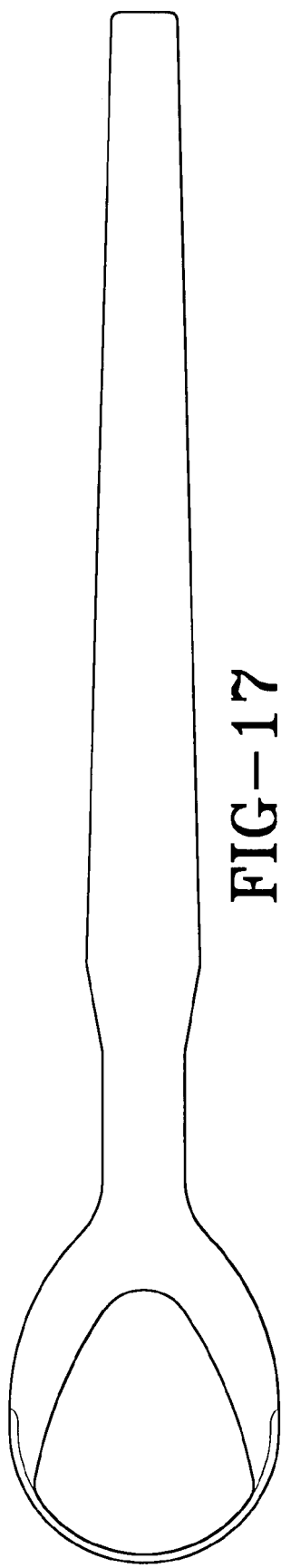
FIGS. 17–22 are schematic top plan views of tongue cleaning devices having flexible handles.

In FIG. 16, material is removed from the interior of both the head and the handle as indicated by the shaded area 120.

Figure 20:
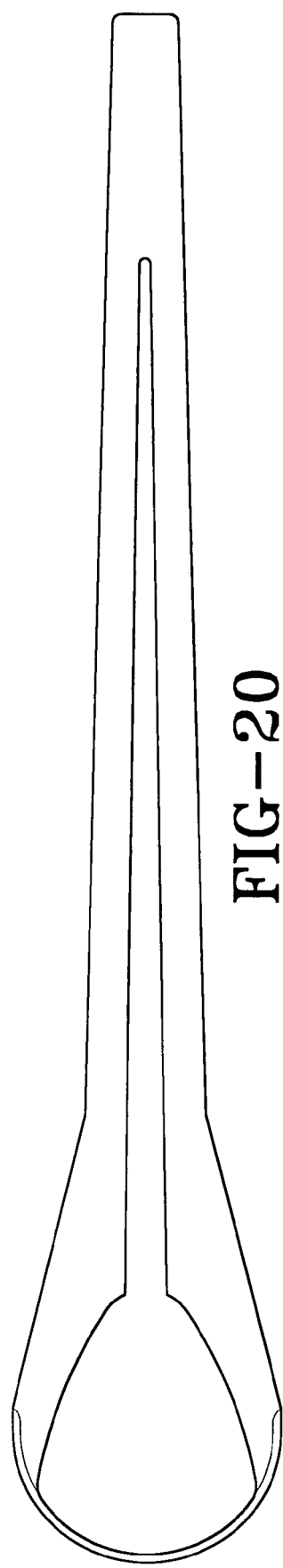
Figure 21:
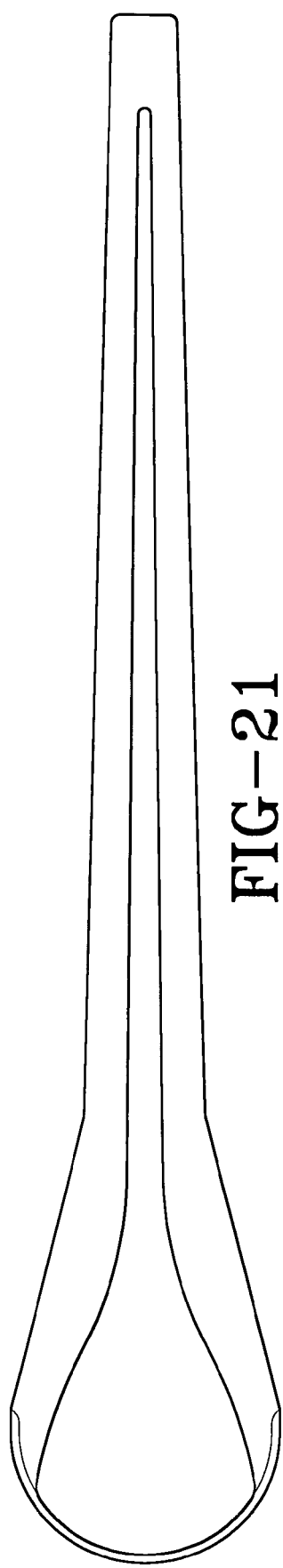
Figure 22:
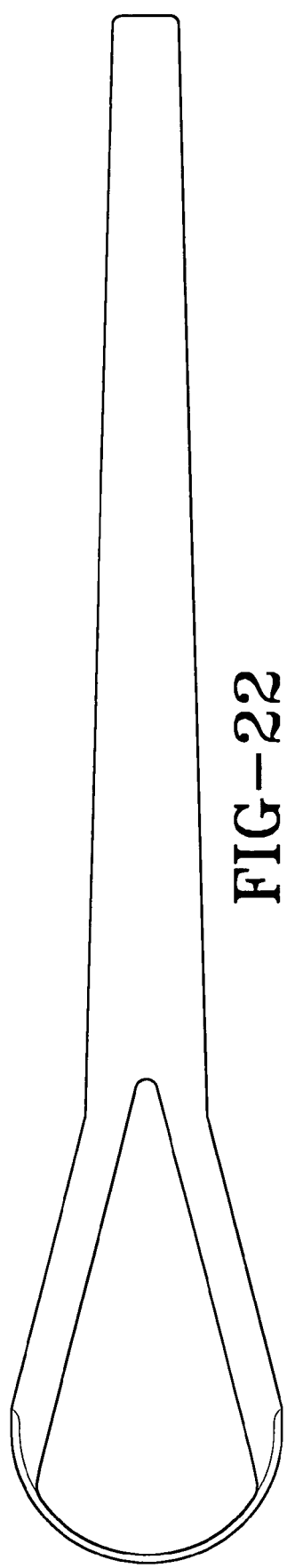

The removal of the material in the center of the tongue cleaning device increases the flexibility of the device. The length of the material removed from the center of the device may extend halfway down the handle as depicted in FIG. 16, substantially the entire length of the handle as depicted in FIGS. 20 and 21, or a small amount of the handle as depicted in FIG. 22.

Figure 18:
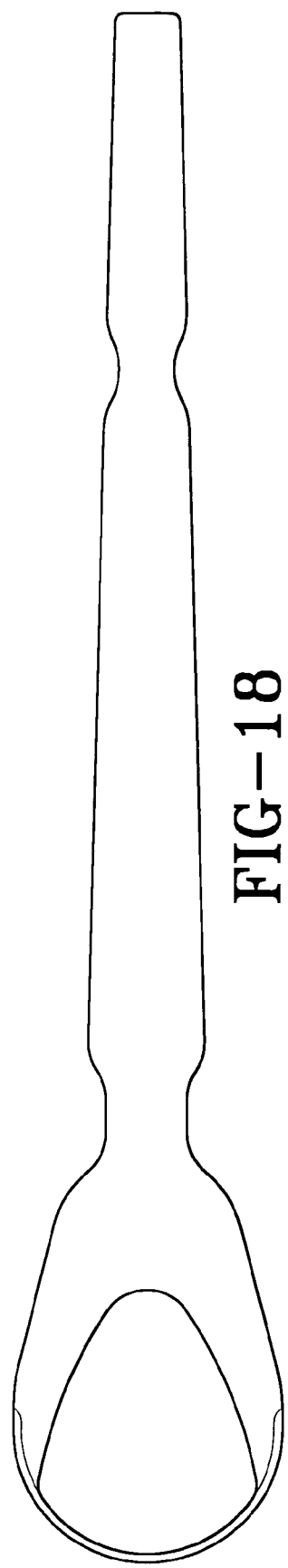
Figure 19:
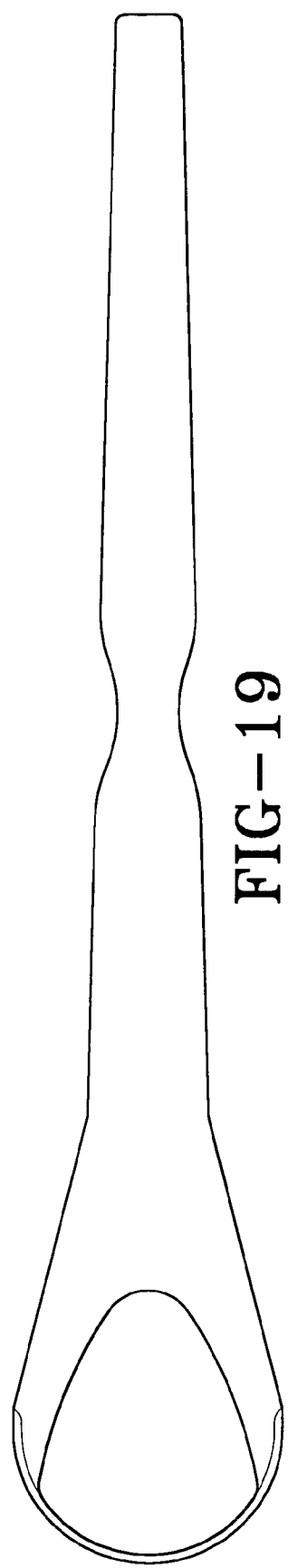

FIGS. 17–22 show additional handle shapes that increase the flexibility of the head with respect to the handle. In FIG. 18, two spaced-apart, indented portions are used to allow the handle to flex at two positions. This configuration allows the user to hold the end of the handle in the palm of his hand and bend the middle portion of the handle is conform with his palm.

In each of the embodiments described above and below, the head or entire body of the tongue cleaning device may be fabricated from titanium or a titanium alloy. Creating tongue cleaning devices from titanium or a titanium alloy provides the tongue cleaning devices with advantages not known before in the art of tongue cleaning devices. Titanium is hypo-allergenic and may be repeatedly applied against the user's tongue without creating a reaction between the saliva and the titanium. Titanium will not react with the debris on the tongue.

Titanium allows the tongue cleaning devices to be flexible while having a memory so that the devices return to their original shape after each use. The flexibility of titanium tongue cleaning devices allows the devices to be safer and less rigid than those in the prior art. The flexible tongue cleaning devices allow the working bodies of the tongue cleaning devices to adjust to the contours of the tongue. The use of titanium allows the user to apply force to the tongue while allowing the handle of the tongue cleaning device to flex to prevent the user from applying too much force to the tongue.

Tongue cleaning device handles fabricated from titanium have an inherent memory quality that will revert to their original shapes after being bent. Handles fabricated from plastic can break after frequent uses and handles fabricated from steel will bend out of shape after frequent uses.

Another advantage of using titanium with a tongue cleaning device is that the tongue cleaning device may be provided with a color while not coating or painting the device. Coatings and painted surfaces may be undesired by some users because of allergic reactions, or the fear that the coating may come off in the user's mouth. Titanium can be colored by anodizing the outer surface of the titanium. Anodized titanium is hypo-allergenic and no paints, pigments, or dyes are used to create the colored appearance. The colored appearance of the titanium is generated by creating a transparent oxide film on the outer surface of the metal tongue cleaning device. The film appears colored to the user because light striking the surface is partially reflected by the film and partially passes through the film to reflect off of the metal below the film. The delayed light reflection combined with the surface light reflection to provide a colored appearance to the user. The thickness of the oxide film determines the color viewed by the user.

A titanium tongue cleaning device may thus be colored to allow different users in the same household a way to readily identify their tongue scraper from another user's. Colored cleaning devices are also desired for marketing and advertising purposes. Anodizing the titanium in this manner provides the identifying color feature while not using dyes, paints, or coatings.

FIGS. 23A though 23X depict different cross sections for the scraping wall and working edge of the tongue cleaning device. These cross sectional shapes may be used with any of a variety of tongue cleaning device configurations such as the configurations depicted in FIGS. 1–22 and those depicted in U.S. Pat. Nos. 5,916,228 and 5,893,860.

Each of the scraping member configurations depicted in FIG. 23 has a curved or rounded working edge configured to effectively remove debris from the tongue while not catching on or snagging on the tongue. Each configuration has a rounded lower surface wherein the angle included by the curve of the rounded surface is large enough to maintain the rounded surface in contact with the tongue when the handle of the tongue cleaning device is pivoted upwardly with respect to the user's face. In all of the embodiments except FIGS. B and Q, the included angle is at least 180 degrees. In FIGS. B and Q, the included angle is greater than 90 degrees and is shown to be 135 degrees (FIG. B) and 150 degrees (FIG. Q).

The rounded working edge of each configuration has an equal thickness or a smaller thickness than the maximum thickness of the scraping member. The working edge may be positioned along the cross section centerline of the scraping member as depicted in FIGS. 23F, I, J, K, M, and N. The working edge may also be positioned toward the forward end of the scraping member as depicted in FIGS. 23A, B, C, D, E, G, H, L, O, P, Q, R, and S. In other embodiments, the working edge is position adjacent the rear end of the scraping member as depicted in FIG. 23T (although any of the above configurations may be reversed). In FIGS. 23U, V, W, and X, the entire scraping member has a curved cross section with the scraping member being concave when viewed from the forward end toward the rear end.

The lower portion of each scraping member shown in FIG. 23 may be described as beaded or tear drop (having a thin neck as shown in FIGS. 23A, C, D, E, F, G, H, I, K, L, M, N, O, P, S, T, U, and X) or rounded (no neck portion as shown in FIGS. B, J, Q, R, V, and W). In the past, the lower portion of the scraping member was essentially square or semi-circular.

The working edge of these figures may be formed by extruding the scraping member to have the shape, hot or cold rolling the member, or welding a piece onto the member to form the shape. The scraping member may be fabricated from stainless steel, titanium, aluminum, copper, or an alloy including one of these materials. Plastic may also be used.

FIGS. 24 and 25 show how one of the scraping members of FIG. 23 having a debris retention recess 300 may be used with a tongue cleaning device 302. Recess 300 is positioned adjacent working edge 304 so that debris gathered up from the tongue is retained in recess 300. Recess 300 is particularly useful for cleaning the tongue of persons in bed so that the debris does not fall off of the device before it can be properly disposed.

Recess 300 is a depressed, concave area defined by the scraping wall of device 302. Debris is gathered up into this concave recess where it is retained until washed out by the user or vigorously shaken loose. FIG. 24 shows an embodiment where the head of the device has a central opening. FIG. 25 shows an embodiment with a closed head.

FIG. 26 depicts an embodiment of the tongue cleaning device wherein the working edge 350 is concave with respect to the tongue 352. Most human tongues 352 have an upper surface that has a pair of side-by-side lobes. Despite this fact, known tongue scraping surfaces have been flat or convex with respect to the tongue. The concave working edge 350 allows the cleaning device to engage a wider area of tongue 352 than flat or convex working edges because the concave working surface better matches the shape of the lobes as depicted in the drawings.

Working edge 350 has a width that extends between opposed edges of the head. The height of the scraping wall is taller at the edges than in the middle portion while the upper surface is substantially coplanar. In the preferred embodiment, the concave surface is a smooth curve. The scraping wall may have any of the shapes depicted in FIG. 23.

FIGS. 28–30A depict different steps in a method of manufacturing a scraping wall for a tongue cleaning device so that the working edge of the wall is not too sharp while being sharp enough to clean the surface of the tongue. The rough scraping wall 400 depicted in FIG. 28 has an upper section 402 of a first thickness 403 and a lower section 404 of a second thickness 405. Second thickness 405 has a dimension of between 0.010 to 0.032 inches with preferred dimensions being between 0.012 and 0.020 inches. A working edge having dimensions in this range have been found to be good at cleaning the tongue while not cutting the tongue.

In FIG. 29, the arrows indicated by the numeral 410 are used to indicate polishing action that is taken to smooth the sharp edges of scraping wall 400 to form a polished wall 412. Wall 412 has the lower section formed with the proper dimensions even though a portion of its lower edge is completely worn away. Various polishing methods may be used to round these corners.

Figure 31:
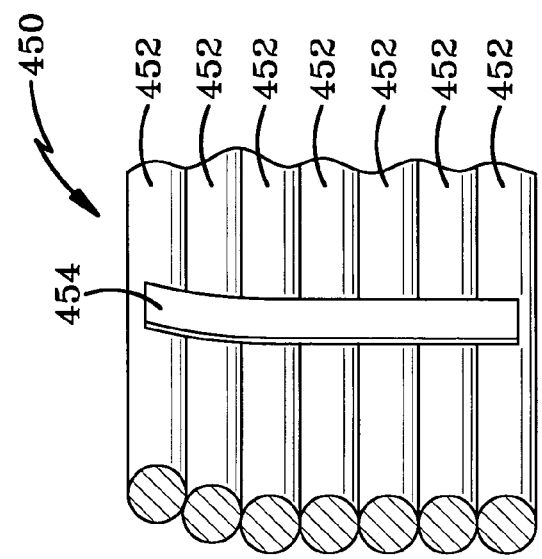
FIG. 31 is a section view of a scraping wall formed with a plurality of wires.

In FIG. 31, a scraping head 450 is shown that is manufactured from a plurality of stacked wires 452. Head 450 may be in any of a variety of shapes known in the art. One exemplary shape is shown in FIG. 1. Wires 452 are connected together with binding strips 454 or may be welded together or otherwise bonded together. Each wire 452 has a known diameter of between 0.010 inches and 0.032 inches with a preferred dimension between 0.012 and 0.020 inches. Wires 452 are available from supplies at these known dimensions and are already rounded. Wires 452 thus do not need polished to be smooth to prevent the risk of cutting.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

What is claimed is:

1. A tongue cleaning device that is used for removing debris from a tongue; the device comprising:
    a body having a handle and head;
    the head having a scraping wall defining a working edge adapted to be moved over the tongue; the scraping wall having a front surface facing in the direction of the handle of the body; and
    the head of the body defining a debris retention recess adapted to collect debris as it is removed from the tongue by the working edge; the debris retention recess being a depression defined in the front surface of the scraping wall.

2. The device of claim 1, wherein the debris retention recess is adjacent the working edge.

3. The device of claim 2, wherein the debris retention recess is a curved depression defined by the head of the body.

4. The device of claim 1, wherein the working edge is concave with respect to the tongue; the scraping wall having a middle and a pair of edges; the scraping wall having a first height at the edges and a second height at the middle; the first height being larger than the second height to define the concave working edge.

5. The device of claim 1, wherein the body is fabricated from titanium.

6. A head for a tongue cleaning device that is used for removing debris from a tongue; the head comprising:
   a body having a scraping wall having an upper edge and a lower edge; the lower edge defining a working edge adapted to be moved over the tongue; and
   the body defining a debris retention recess adapted to collect debris as it is removed from the tongue by the working edge; the debris retention recess being a depression defined in the scraping wall between the upper and lower edges of the scraping wall.

7. The device of claim 6, wherein the debris retention recess is adjacent the working edge.

8. The device of claim 7, wherein the debris retention recess is a curved depression defined by the head of the body.

9. The device of claim 6, wherein the working edge is concave with respect to the tongue; the scraping wall having a middle and a pair of edges; the scraping wall having a first height at the edges and a second height at the middle; the first height being larger than the second height to define the concave working edge.

10. The device of claim 6, wherein the body is fabricated from titanium.

11. A head for a tongue cleaning device that is used for removing debris from a tongue; the head comprising:
    a body having a scraping wall defining a working edge adapted to be moved over the tongue; and
    the scraping wall of the body defining a debris retention recess adapted to collect debris as it is removed from the tongue by the working edge; the debris retention recess disposed immediately above the working edge; the debris retention recess being entirely defined by the scraping wall.

12. The device of claim 11, wherein the debris retention recess is a curved depression defined by the head of the body.

13. The device of claim 11, wherein the working edge is concave with respect to the tongue; the scraping wall having a middle and a pair of edges; the scraping wall having a first height at the edges and a second height at the middle; the first height being larger than the second height to define the concave working edge.

14. The device of claim 11, wherein the body is fabricated from titanium.

* * * * *